US008621954B1

(12) United States Patent
Dellon et al.

(10) Patent No.: US 8,621,954 B1
(45) Date of Patent: Jan. 7, 2014

(54) SYSTEMS AND METHODS FOR GRAVITY COMPENSATION (75) Inventors: Brian Dellon, Seattle, WA (US); Yoky Matsuoka, Palo Alto, CA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 322 days.

(21) Appl. No.: 13/153,614

(22) Filed: Jun. 6, 2011

Related U.S. Application Data (60) Provisional application No. 61/351,397, filed on Jun. 4, 2010.

(51) Int. Cl.
*F16H 1/00* (2006.01)

(52) U.S. Cl.
USPC .................. 74/490.01; 74/490.02; 901/48

(58) Field of Classification Search
USPC .............. 74/490.01, 490.02, 490.03, 490.04, 74/490.05, 490.06; 901/48
See application file for complete search history.

(56) References Cited

U.S. PATENT DOCUMENTS

| 5,423,648 | A | * | 6/1995 | Akeel et al. ................ 198/468.2 |
| 5,569,328 | A | * | 10/1996 | Petvai et al. ................ 118/696 |
| 5,667,186 | A | * | 9/1997 | Luber et al. ................ 248/550 |
| 5,697,757 | A | * | 12/1997 | Lindsay ................ 414/744.6 |
| 6,354,167 | B1 | * | 3/2002 | Snow ................ 74/490.01 |
| 7,683,564 | B2 | * | 3/2010 | Harris et al. ................ 318/565 |
| 7,828,162 | B2 | * | 11/2010 | Wiesbauer ................ 212/297 |
| 7,971,503 | B2 | * | 7/2011 | Nakamura ................ 74/490.01 |
| 8,077,212 | B2 | * | 12/2011 | Chapman ................ 348/208.7 |
| 8,181,662 | B2 | * | 5/2012 | Pollack et al. ................ 137/15.08 |
| 8,240,973 | B2 | * | 8/2012 | Xu et al. ................ 414/799 |
| 8,251,599 | B2 | * | 8/2012 | Chapman ................ 396/428 |

OTHER PUBLICATIONS

An, J. et al., "In haptics, the influence of the controllable physical damping on stability and performance," in Proc. IEEE Int. Conf. Intell. Robots Syst., 2004, vol. 2, pp. 1204-1209.
Blauer, M. et al., "State and parameter estimation for robotic manipulators using force measurements," IEEE Trans. Automat. Control, vol. AC-32, No. 12, pp. 1055-1066, Dec. 1987.
Calafiore, G. et al., "Robot dynamic calibration: Optimal excitation trajectories and experimental parameter estimation," J. Robot. Syst., vol. 18, No. 2, pp. 55-68, 2001.
Colgate, J. E. et al., "Cobots: Robots for collaboration with human operators," in Proc. IMECE, 1996, pp. 433-439.

(Continued)

*Primary Examiner* — David M Fenstermacher
(74) *Attorney, Agent, or Firm* — McDonnell Boehnen Hulbert & Berghoff LLP (57) ABSTRACT Disclosed herein are systems and methods that may compensate for the effect of gravity on certain haptic devices, such as haptic-robot devices. An example embodiment of the disclosed systems and methods may take the form of a gravity-compensation system that includes (a) a carriage coupled to a rod having a first axis, wherein the carriage is configured to move along the first axis, (b) a displacement mechanism coupled to the carriage, wherein the displacement mechanism is configured to move the carriage along the first axis of the rod based on a displacement of an extendable arm along the first axis, and (c) a restorative-force mechanism configured to exert, on the carriage, a restorative force that acts along a second axis. The gravity-compensation system acts in a primarily passive manner, helping to ensure the safety of users at the point of human-robot interaction (pHRI).

20 Claims, 8 Drawing Sheets

(56) References Cited

OTHER PUBLICATIONS

Dellon, B. et al., "Feedback distortion to augment controllability of human limb motion," in Proc. Virtual Rehabil., 2008, pp. 22-27.

Dellon, B. et al., "Path guidance control for a safer large scale dissipative haptic display," in Proc. IEEE Int. Conf. Robot. Autom., 2008, pp. 2073-2078.

Delta Haptic Device, Force Dimension. (2009). [Online]. Available: http://www.forcedimension.com.

Gretton, A. et al., "Support vector regression for black-box system identification," in Proc. IEEE Signal Process. Workshop Statist. Signal Process., 2001, pp. 341-344.

Janot, A. et al., "Modeling and identification of a 3 DOF haptic interface," in Proc. IEEE Int. Conf. Robot. Autom., 2007, pp. 4949-4955.

Julier, S. J. et al., "A new approach for filtering nonlinear systems," in Proc. Amer. Control Conf., 1995, vol. 3, pp. 1628-1632.

Laopoulous, T. et al., "Microcontroller-based measurement of angular position velocity and acceleration," in Proc. IEEE Instrum. Meas. Conf., 1996, pp. 73-77.

Loureiro, R. et al., "Using haptics technology to deliver motivational therapies in stroke patients: Concepts and initial pilot studies," in Proc. Eurohaptics, Birmingham, U.K., 2001, pp. 1-6.

Lum, P. S. et al., "The use of a robotic device for post-stroke movement therapy," in Proc. Int. Conf. Rehabil. Robot., Bath, U.K., Apr. 14-15, 1997.

Iurian, C. et al., "Identification of a system with dry friction," Inst. d'Org. i Control de Sistemes Ind., Univ. Polit'ecnica de Catalunya, Barcelona, Spain, Tech. Rep., 2005.

Masri, S. F. et al., "Structure-unknown non-linear dynamic systems: Identification through neural networks," Smart Mater. Struct., vol. 1, pp. 45-56, 1992.

Matsuoka, Y. et al., "Design of life-size haptic environments," in Experimental Robotics VII, D. Rus and S. Singh, Eds. London, U.K.: Springer-Verlag, 2001, pp. 461-470.

PHANTOM Premium 3.0 Haptic Device, Sensable Technologies, Inc. (2009). [Online]. Available: http://www.sensable.com.

Rahman, T. et al., "A simple technique to passively gravity-balance articulated mechanisms," ASME Trans. Mech. Des., vol. 117, No. 4, pp. 655-658, 1995.

Reed, M. R. et al., "Modeling and control of an improved dissipative passive haptic display," in Proc. IEEE Int. Conf. Robot. Autom., 2004, vol. 1, pp. 311-318.

Richard, C. et al., "Friction identification for haptic display," in Proc. ASME, Dyn. Syst. Control Div., 1999, vol. 67, pp. 327-334.

Salisbury, K. et al., "Preliminary design of a whole-arm manipulator system (WAMS)," in Proc. IEEE Int. Conf. Robot. Autom., 1988, vol. 1, pp. 254-260.

Swanson, D. K. et al., "Path-following control for dissipative passive haptic displays," in Proc. 11th Symp. Haptic Interfaces Virtual Environ. Teleoperator Syst., 2003, pp. 101-108.

Tahmasebi, A. M. et al., "Dynamic parameter identification and analysis of a PHANToM haptic device," in Proc. IEEE Conf. Control Appl., 2005, pp. 1251-1256.

Tam, S. et al., "A system identification technique for haptic devices," in Proc. IEEE Conf. Control Appl., 2005, pp. 1240-1245.

Van Der Linde, R. Q. et al., "The HapticMaster, a new high-performance haptic interface," in Proc. Eurohaptics, Edinburgh, U.K., 2002, pp. 1-5.

Van Der Merwe, R. et al., "The square-root unscented Kalman filter for state and parameter estimation," in Proc. Int. Conf. Acoust., Speech, Signal Process., 2001, pp. 3461-3464.

WAM robot, Barrett Technology, Inc. (2009). [Online]. Available: http://www.barett.com.

Wan, E. A. et al., "The unscented Kalman filter for nonlinear estimation," in Proc. IEEE Adaptive Syst. Signal Process., Commun., Control Symp., 2000, pp. 153-158.

* cited by examiner

SYSTEMS AND METHODS FOR GRAVITY COMPENSATION

RELATED APPLICATIONS

This application claims priority to U.S. Provisional Patent Application Ser. No. 61/351,397 filed Jun. 4, 2010, entitled Method of Gravity Compensation, which is incorporated herein in its entirety.

STATEMENT OF U.S. GOVERNMENT INTEREST

This invention was made with U.S. Government support under grant number 0238204 awarded by the National Science Foundation. The U.S. Government has certain rights in the invention.

BACKGROUND

Haptic technology is a tactile-feedback technology that, in response to user inputs at a haptic device, applies forces to the user or otherwise controls the user's interaction with the device. The applied forces may be used, for example, to assist in the creation and control of virtual objects. General-purpose haptic devices are commonly used as an assistive technology to enhance a human's interaction within a virtual environment. Applications of haptic devices within virtual environments include, but are not limited to, video games, training surgical procedures, training sports techniques, or physical rehabilitation. Haptic devices commonly take the form of a robot, in which case the point at which a human interacts with such haptic devices may be referred to as the point of physical human-robot interaction (pHRI).

In designing haptic devices, the safety of the human user must be considered, especially at the point of pHRI. To minimize safety concerns, haptic devices today are commonly limited in size. Additionally, haptic devices today commonly utilize software-based safety mechanisms to control large inertia and energetic mechanical components.

As the field of haptic devices continues to evolve, the size of pHRI environments continue to grow. Large pHRI environments may include, as one example, physical rehabilitation environments that are commonly used by users who are weak, disabled, or have a hard time coordinating their limbs. Large pHRI environments may also include, as another example, video-game environments that are commonly used by users that are highly physical and strong, and that therefore may push the limits of haptic devices. Other examples of large pHRI environments may exist as well, with more examples coming into existence every day as haptic technology is increasingly incorporated into various applications.

However, as the size of pHRI environments continue to grow, so too does the size of haptic-device components at the point of pHRI. Such components are increasingly larger and/or are capable of moving with greater forces at the point of pHRI. Accordingly, it has become increasingly difficult to ensure the safety of such pHRI environments at least because such pHRI environments involve components that are capable of moving with relatively high energy and intertia. Such high-energy and high-intertia components may exhibit undesirable forces at the point of pHRI which may at best degrade the user's experience, and may at worst present safety concerns In particular, it has become increasingly difficult to control large pHRI environments having energetic or high-inertial components with software-based safety mechanisms alone.

This is at least because software-based safety mechanisms generally involve active control of components at the point of pHRI. Such active control commonly involves use of electro-mechanical components that, if controlled incorrectly, may pose safety concerns of their own at the point of pHRI. Therefore, there is increasing interest in the development of more effective systems and methods for removing undesirable forces at the point of pHRI, and thereby improving safety and user-experience.

SUMMARY OF THE INVENTION

In a haptic device, one example of an undesirable force that may act at the point of physical human-robot interaction (pHRI) is a force due to gravity on mechanical elements of the haptic device. Indeed, as large mechanical elements of a haptic device move, the force due to gravity on such mechanical elements may vary. Such a variation in the force due to gravity may result in uncontrollable, or otherwise unsafe, movement of the mechanical elements at the point of pHRI. Thus, the safety of haptic devices may be improved by systems and methods that compensate for such undesirable effects of gravity (i.e., systems and methods for gravity compensation).

Common systems and methods for gravity compensation involve active components that counteract gravity. For example, such systems and methods may include electro-mechanical components that are driven by software to act opposite gravity. However, such active components themselves present safety concerns, as there is always the chance that such components may be driven in an unpredictable, unstable, or otherwise generally unsafe manner. In other words, with active elements, there is a risk that the user may be exposed to an unstable (and potentially large and/or dangerous) element at the point of pHRI. For at least this reason, systems and methods for gravity compensation that involve passive elements that counteract gravity may be more desirable.

Disclosed herein are systems and methods for gravity compensation involving primarily passive components, such as dissipative components that dissipate or redirect forces due to gravity. These passive components may provide for gravity compensation without requiring electro-mechanical components that are driven by software to act opposite forces due to gravity. Although the systems and methods for gravity compensation disclosed herein are discussed as capable of being implemented within haptic devices, it should be understood that this is not necessary. Aspects of the systems and methods for gravity compensation disclosed herein may be applied in a variety of other devices and/or contexts.

In an implementation, the disclosed gravity-compensation systems and methods may be applied to counteract the force due to gravity in a haptic device having a prismatic joint with an extendable arm. In such a haptic device, the extendable arm may be capable of moving in and out of a housing of the prismatic joint, and the prismatic joint itself may also be capable of rotating both horizontally and vertically. As a result, the force due to gravity on the prismatic joint of the haptic device may vary. To counteract such a varying force due to gravity, a disclosed gravity-compensation system may be coupled to the prismatic joint such that it may apply a dissipative, resistive, force that acts opposite the force due to gravity.

For instance, the disclosed gravity-compensation system may include a carriage and rod configuration that is attached to a housing of the prismatic joint, and the resistive force that acts opposite the force due to gravity may be applied to the carriage. The carriage may be moved along the rod, proportional to a displacement of the extendable arm, thus changing the point at which the resistive force acts on the prismatic joint. In this way, the amount of resistive force applied by the gravity-compensation mechanism is continuously adjusted to account for a changing center of gravity of, and thus changing force due to gravity on, the prismatic joint as the extendable arm is moved.

A first embodiment of the disclosed systems and methods may take the form of a gravity-compensation system that includes (a) a carriage coupled to a rod having a first axis, wherein the carriage is configured to move along the first axis, (b) a displacement mechanism coupled to the carriage, wherein the displacement mechanism is configured to move the carriage along the first axis of the rod based on a displacement of an extendable arm along the first axis, and (c) a restorative-force mechanism configured to exert, on the carriage, a restorative force that acts along a second axis.

In an aspect of the first embodiment, the restorative-force mechanism may include (i) a cable having a first end that is coupled to the carriage and a second end that is coupled to a gearing mechanism and (ii) a resistive-force mechanism coupled to the gearing mechanism. The gearing mechanism may include (i) a first gear, where the second end of the cable is coupled to the first gear and (ii) a second gear coupled to the first gear and the resistive-force mechanism.

In another aspect of the first embodiment, the resistive-force mechanism may include at least one of a spring mechanism and a pneumatic mechanism. The spring mechanism may include at least one of a constant-force spring and a torsion spring.

A second embodiment of the disclosed systems and methods may take the form of a method that includes (a) moving a carriage along a first axis of a rod based on a displacement of an extendable arm along the first axis and (b) exerting, on the carriage, a restorative force that acts along a second axis. Such a method may be carried out by the gravity-compensation system described above.

These as well as other aspects and advantages will become apparent to those of ordinary skill in the art by reading the following detailed description, with reference where appropriate to the accompanying drawings.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

I. INTRODUCTION

Described herein are aspects of systems and methods for gravity compensation that may be applied in a variety of devices and/or contexts, including in certain haptic devices. An embodiment of the present gravity-compensation system accounts for changes in force due to gravity in a primarily passive manner. Further, in an embodiment, the gravity-compensation system may be implemented using low-inertia components that may account for even relatively large changes in force due to gravity in a stable manner. As a result, the gravity-compensation system described herein may be employed to improve the safety and stability of even large haptic devices at the point of physical human-robot interaction (pHRI).

In an implementation, the disclosed gravity-compensation system may be employed in a haptic device having a prismatic joint that includes a housing and an extendable arm. In such a haptic device, as the arm is extended in one direction or the other, the torque on the arm due to gravity may change as a result of, at least, a corresponding change in the center of gravity and moment arm of the prismatic joint. The torque may be an undesirable force that acts on the haptic device at the pHRI and the disclosed gravity-compensation system may counteract such an undesirable force.

II. Exaple System

For purposes of context and explanation only, an example haptic device that incorporates the disclosed gravity-compensation system is discussed briefly below. However, it should be understood that the disclosed gravity-compensation system described herein may be utilized in other systems and/or contexts, including other haptic devices. Thus, the example haptic device discussed below should be understood to be but one example of a haptic device in which the disclosed gravity-compensation system may be utilized, and therefore should not be taken to be limiting.

a. Example Haptic Device

Figure 1:
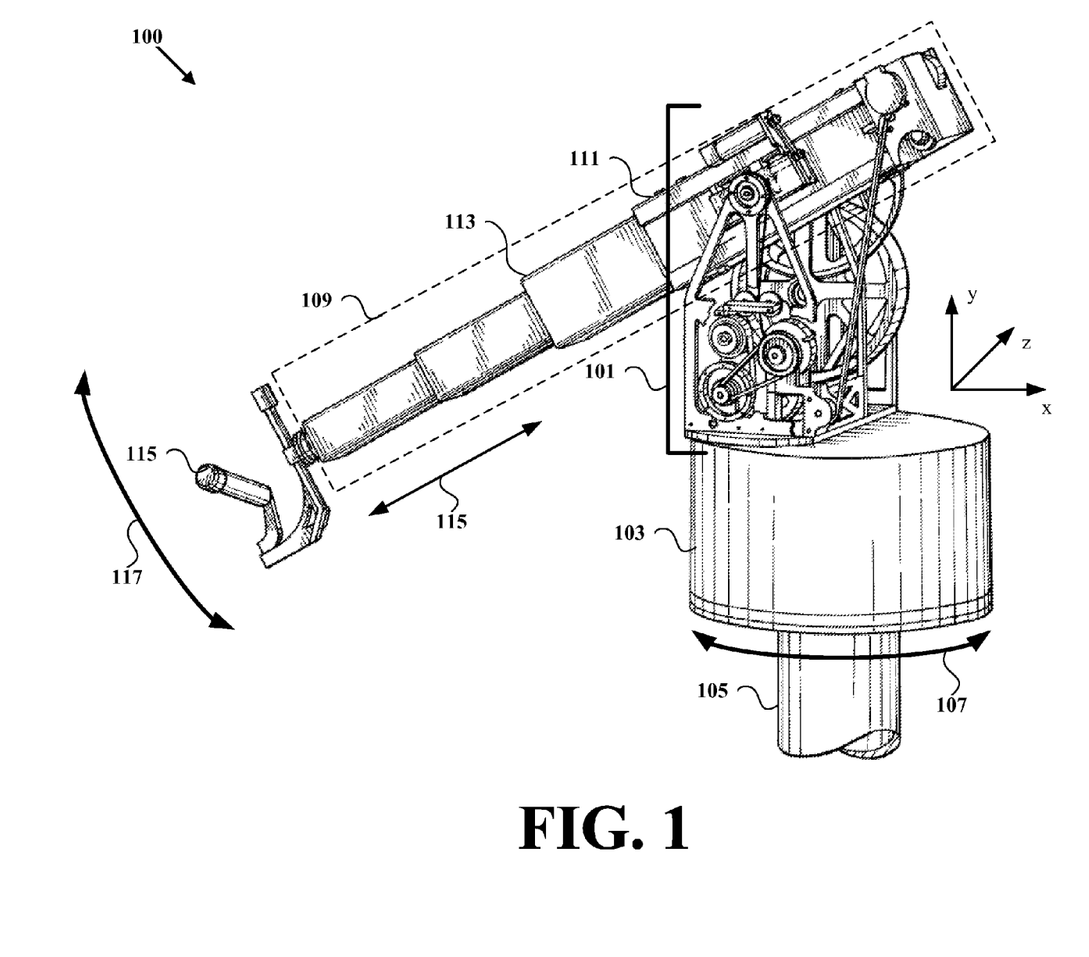
FIG. 1 depicts an example haptic device that includes an example gravity-compensation system, in accordance with an embodiment.

FIG. 1 depicts an example haptic device 100 that includes an example gravity-compensation system 101, in accordance with an embodiment. As shown, gravity-compensation system 101 is coupled to a turret 103 which, in turn, sits atop a base 105. Turret 103 may be configured to swivel, or to be generally rotatable throughout the x-z plane, as indicated by motion arrows 107.

Gravity-compensation system 101 may also be coupled to a prismatic joint 109. Prismatic joint 109 may be coupled to the top of gravity-compensation system 101 such that turret 103, by way of gravity-compensation system 101, provides a stage for rotation of prismatic joint 109. For example, gravity-compensation system 101 may be rigidly attached to a top surface of turret 103. Further, prismatic joint 109 may be attached to gravity-compensation system 101 by way of a joint that is oriented with the x-z plane such that prismatic joint 109 may also be rotatable through the x-y plane.

Prismatic joint 109 includes an extendable arm 113 which is generally extendable through an interior of a housing 111 of prismatic joint 109. Extendable arm 113 may be generally configured such that a handle 115, coupled to extendable arm 113, is movable towards, and away from, housing 111. In other words, extendable arm 113 may be moved to and from housing 111, as indicated by motion arrows 117. Note that extendable arm 113 is shown as a telescoping arm that may be collapsed inside of housing 111. Although extendable arm 113 is shown as telescoping, a telescoping arrangement of extendable arm 113 is not necessary. As one alternative example, extendable arm 113 may be a non-telescoping arm that is movable into one end of housing 111 and out of another end of housing 111.

As noted, haptic device 100 also includes a handle 115 coupled to extendable arm 113. Generally, handle 115 provides a point of human-robot interaction (pHRI) at which a user may manipulate haptic device 100, such as by pushing and pulling extendable arm 113 (as shown by motion arrows 117), rotating extendable arm 113 in a generally horizontal manner throughout the x-z plane (as shown by motion arrows 107), and/or rotating extendable arm 113 in a generally vertical manner throughout the x-y plane (as shown by motion arrows 119).

Whether extendable arm 113 is a telescoping element or a non-telescoping element, those of skill in the art will appreciate that as extendable arm 113 is extended in and out of housing 111, the center of gravity and/or the moment arm of prismatic joint 109 may vary. As a result, the force of gravity acting on extendable arm 113 (manifested as a torque on extendable arm 113), including the force experienced at handle 115, or the point of pHRI, may vary. In certain applications, such as those applications involving a large pHRI environment as described above, this varying force at the point of pHRI with haptic device 100 may be undesirable. As one example, in a video-game application, it may be desirable to provide a gravity-neutral interface to improve realism. As another example, in a rehabilitation application, it may be desirable to provide a gravity-neutral interface to ensure the safety of a relatively weak user. Accordingly, as described below, gravity-compensation 101 may be implemented so as to minimize, or remove, forces due to gravity at the point of pHRI.

b. Example Gravity-Compensation System

Figure 2:
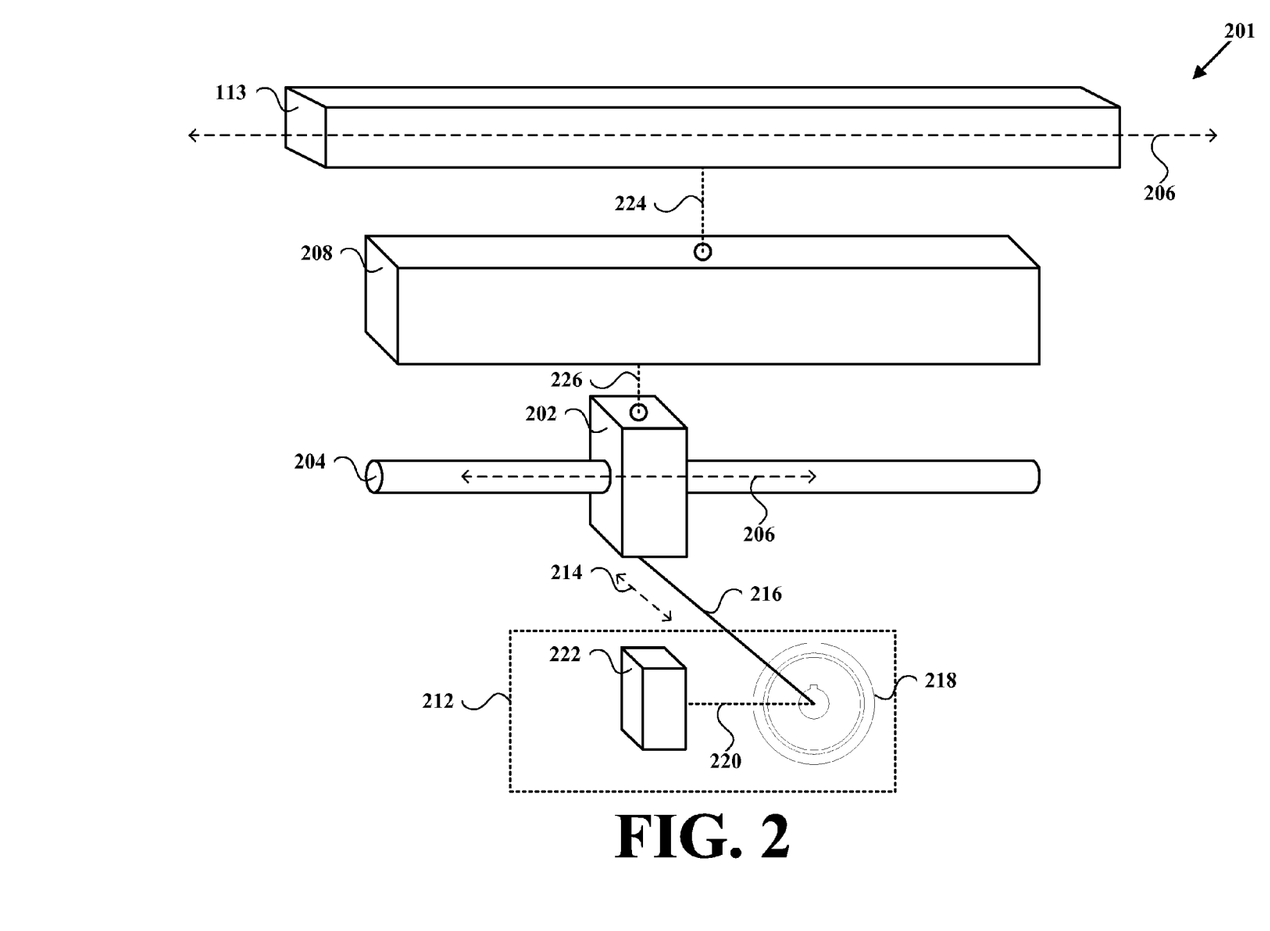
FIG. 2 depicts a simplified block diagram of the example gravity-compensation system, in accordance with an embodiment.

FIG. 2 is a simplified block diagram of an embodiment 201 of a disclosed gravity-compensation system, which may be implemented as part of a larger haptic device (e.g., as is gravity-compensation system 101 of haptic device 100 in FIG. 1). Gravity-compensation system 201 may be implemented in other devices as well.

As shown, gravity-compensation system 201 may include a carriage 202 and a rod 204. Further, Gravity-compensation system 201 may include a displacement mechanism 208 that is coupled to an extendable arm 113 of a device in which gravity-compensation system 201 is implemented. Further still, gravity-compensation system 201 may include a restorative-force mechanism 212, which may include a gearing mechanism 218 and a resistive-force mechanism 222.

Carriage 202 may be generally configured to be movable along a first axis 206 of rod 204. In an example, rod 204 may be a single-start lead screw. Rod 204 may take other forms as well.

Displacement mechanism 208 may be coupled to carriage 202 via interconnect 226. Interconnect 226 may be any suitable interconnect including any mechanical, electrical, wired, or wireless interconnect. In turn, displacement mechanism 208 is also coupled to extendable arm 113, via interconnect 224. Like interconnect 224, interconnect 226 may be any suitable interconnect including any mechanical, electrical, wired, or wireless interconnect. Extendable arm 113 may be movable along first axis 206 and displacement mechanism 208 may be generally configured to move the carriage along first axis 206 of rod 204 based on a displacement of extendable arm 113 along first axis 206.

Displacement mechanism 208 may take any form that provides for movement of carriage 202 along rod 204 based on a displacement of extendable arm 113. In an embodiment, displacement mechanism 208 may include mechanical components that are attached to each of extendable arm 113 and carriage 202, and thereby configured to move carriage 202 along rod 204. In another embodiment, displacement mechanism 208 may include a direct current (DC) motor that is directly and/or indirectly coupled to each of extendable arm 113 and carriage 202, and thereby configured to move carriage 202 along rod 204. In any case, displacement mechanism 208 may be configured to move carriage 202 along rod 204 proportional to a displacement of extendable arm 113.

Carriage 202 may also be coupled to a restorative-force mechanism 212 via an interconnect, which may be a tensioned cable 216. Restorative-force mechanism 212 may be generally configured to exert, on carriage 202, a restorative force that acts along a second axis 214 via cable 216. Such a restorative force may serve to counter-balance a varying center of gravity of prismatic joint 109 as extendable arm 113 is displaced relative to prismatic joint housing 111. Restorative-force mechanism 212 may include a gearing mechanism 218 coupled to a resistive-force mechanism 222 via an interconnect such as a gearing belt 220 or other interconnect. As will be discussed further below, in an example, resistive-force mechanism 222 may include one or more of a spring mechanism and a pneumatic mechanism. Resistive-force mechanism 222 may include other mechanisms as well.

Gravity-compensation system 201 will now be discussed in further detail with reference to FIGS. 3-7, which depict examples of gravity-compensation system 201 from different views. In FIGS. 3-7, like numbers depict like components (unless context dictates otherwise). It should be understood that the examples shown in FIGS. 3-7 are representative only of examples of gravity-compensation system 201, and therefore should not be taken to be limiting. Other components, elements, and devices, including other arrangements thereof, may be used without departing from the spirit or scope of the description contained herein.

Figure 3:
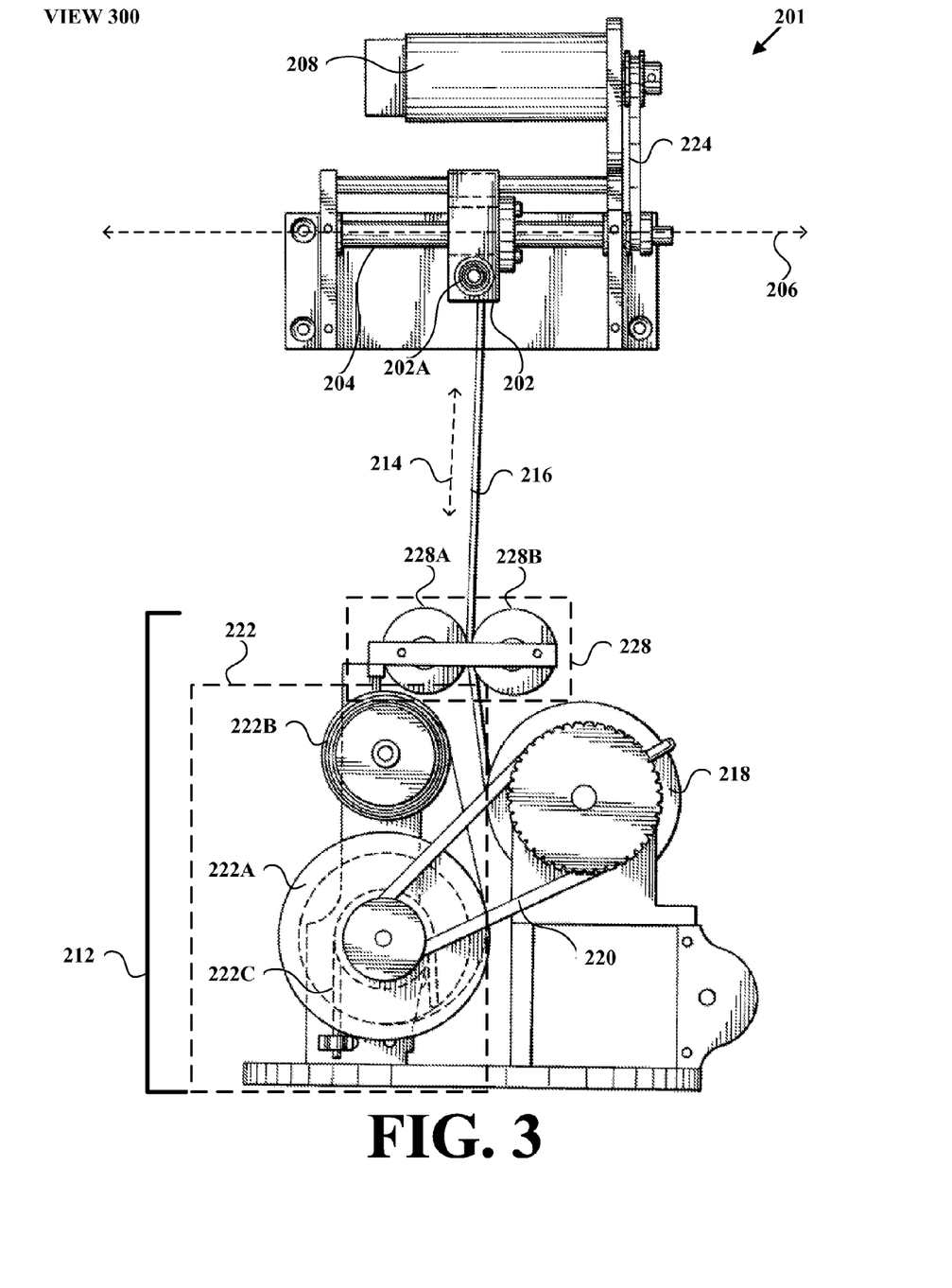
FIG. 3 depicts a first view of the example gravity-compensation system, in accordance with an embodiment.

FIG. 3 depicts a first view 300 of gravity-compensation system 201, according to an example. As shown in view 300, gravity-compensation system 201 includes carriage 202 and rod 204. As noted above, carriage 202 may be generally configured to be movable along first axis 206 of rod 204. Rod 204 is shown as a single-start lead screw that is drivable by displacement mechanism 208, via gearing cable 224. Carriage 202 is shown as coupled to cable 216 at connection point 202A, which may be internal, external, or otherwise affixed to carriage 202. Cable 216 is shown as extending from carriage 202 to restorative-force mechanism 212. An additional view of carriage 202, rod 204, and displacement mechanism 208, is shown in view 700 of FIG. 7.

As shown in view 300, restorative-force mechanism 212 may include a pulley mechanism 228. Pulley mechanism 228 may include one or more pulleys, such as pulleys 228A and 228B. As shown, pulley mechanism 228 may be positioned between carriage 202 and gearing mechanism 218 of restorative-force mechanism 212 in such a way so as to direct the restorative force provided by restorative-force mechanism 212 along axis 214.

As further shown in view 300, gearing mechanism 218 may be coupled to resistive-force mechanism 222 via gearing belt 220. It should be understood, however, that gearing belt 220 may not be necessary, and gearing mechanism 218 and resistive-force mechanism 222 may be coupled in various other direct and/or indirect ways.

Resistive-force mechanism 222 may include a gearing mechanism 222A to which gearing mechanism 218 is coupled. In turn, gearing mechanism 222A may be coupled to a constant-force spring 222B and/or a torsional spring 222C. Each of constant-force spring 222B and/or torsional spring 222C may be arranged to counteract any torsional force applied to gearing mechanism 222A, which force may be exerted by cable 218 on gearing mechanism 218 as a result of movement of carriage 202 along rod 204. An additional view of restorative-force mechanism 212, including resistive-force mechanism 222, is shown in view 600 of FIG. 6.

Although resistive-force mechanism 222 is shown as including gearing mechanism 222A, constant-force spring 222B, and torsional spring 222C, such an arrangement is not necessary. As a general matter, any combination of elements and/or devices that is arranged to counteract a torsional force applied to gearing element 218 may be used. Such other elements and/or devices may include, in addition to spring mechanisms and without limitation, a pneumatic mechanism. Any resistive-force element that provides a sufficiently linear resistive-force response may be used as, or included as part of, resistive-force mechanism 222.

Figure 4:
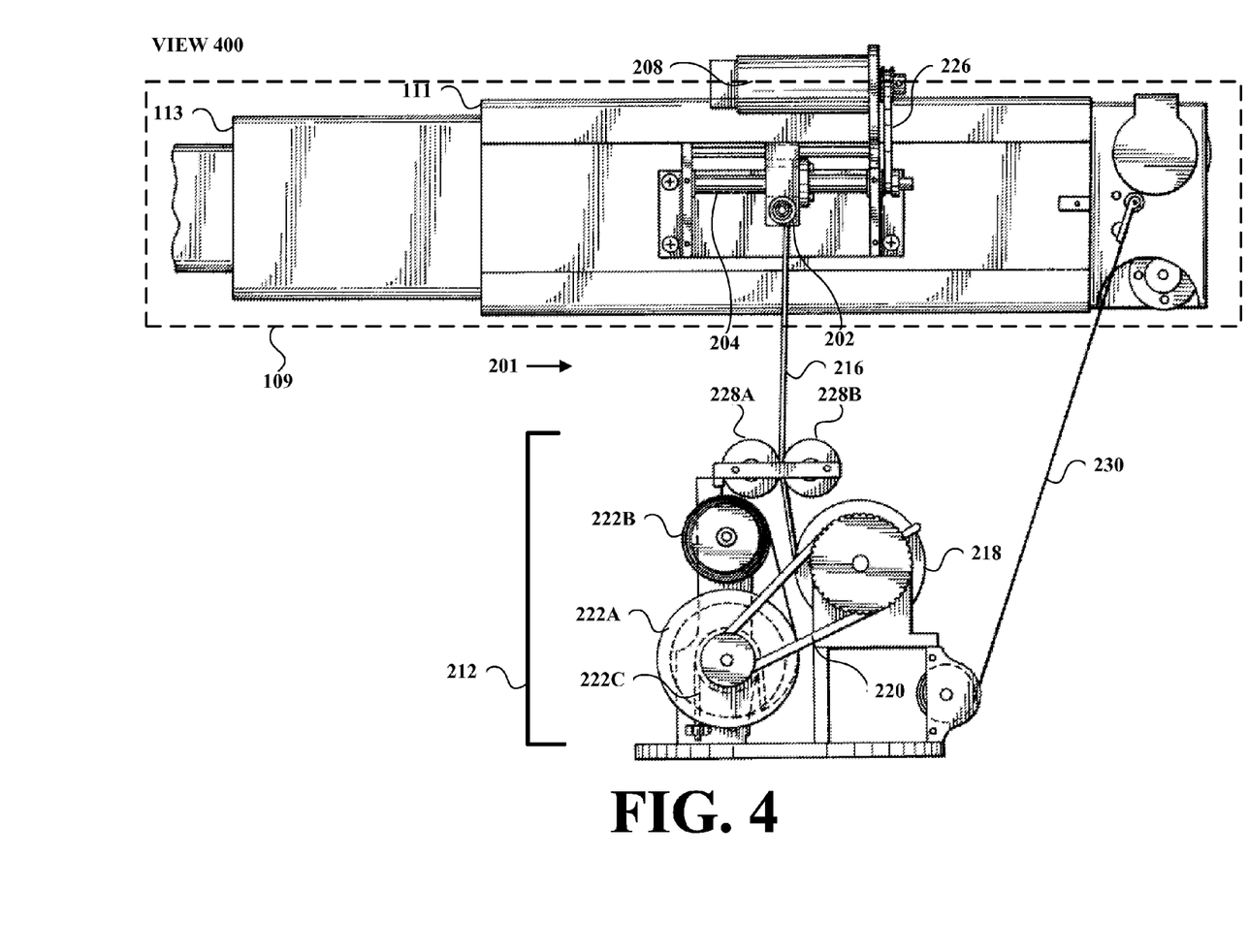
FIG. 4 depicts a second view of the example gravity-compensation system and a prismatic joint, in accordance with an embodiment.

FIG. 4 depicts a second view 400 of gravity-compensation system 201, according to an example. As shown in view 400, carriage 202, rod 204, and displacement mechanism 208 may be attached to an exterior of prismatic joint 109. More specifically, carriage 202, rod 204, and displacement mechanism 208 may be attached to an exterior of housing 111 of prismatic joint 109. Displacement mechanism 208 may be arranged to receive a control signal (or other indication) of the extension of extendable arm 113, so as to responsively move carriage 202 on rod 204. Further, given the location of carriage 202 affixed to prismatic joint 109, any force exerted by restorative-force mechanism 212 via cable 216 will act on prismatic joint 109 so as to ultimately counteract any undesirable torque applied to extendable arm 113 by gravity.

As shown in view 400, a constant-force spring 230 may be coupled at a first end to restorative-force mechanism 212 and coupled at a second end to prismatic joint 109. Constant-force spring 230 is not required, however it may have particular application where extendable arm 113 takes the form of a telescoping extendable arm. This is because, in the event that the telescoping extendable arm is fully extended, the center of gravity of prismatic joint 109 may vary greatly from the center of gravity of prismatic joint 109 when the telescoping extendable arm is not extended. In this way, constant-force spring 230 may provide an independent dissipative force to counteract the torque on extendable arm 113 due to gravity.

Figure 5:
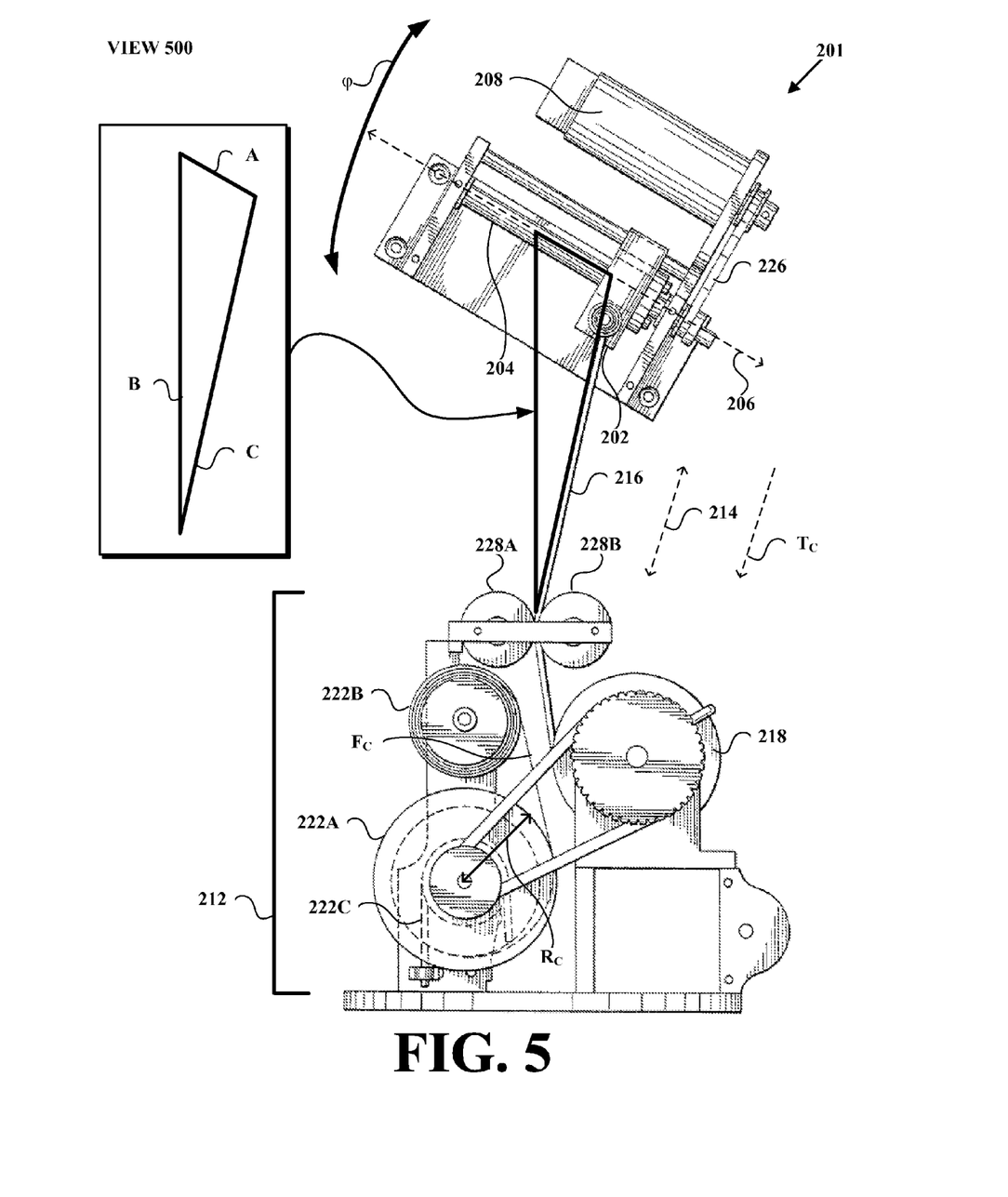
FIG. 5 depicts a third view of the example gravity-compensation system, in accordance with an embodiment.
Figure 6:
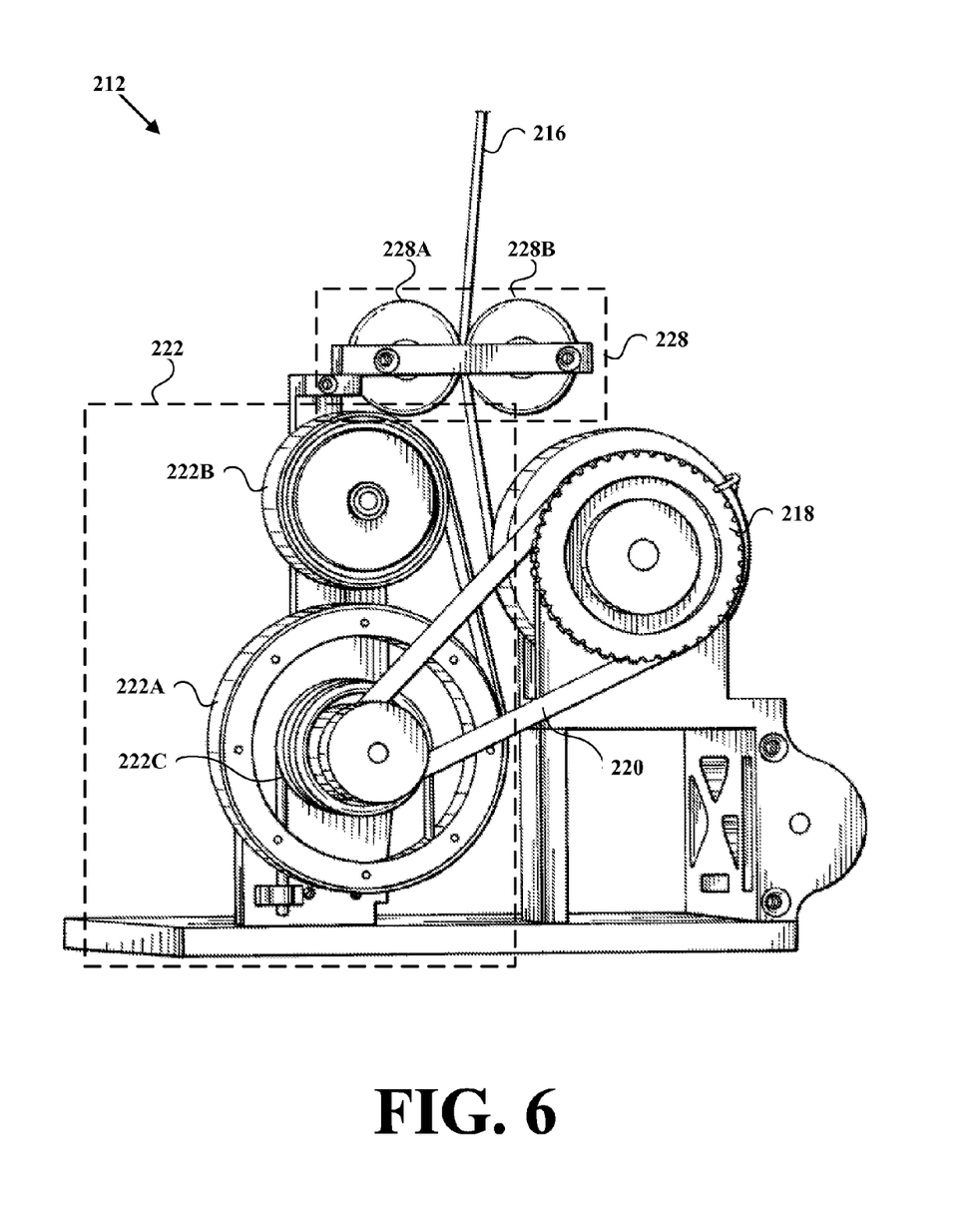
FIG. 6 depicts a restorative-force mechanism of the example gravity-compensation system, in accordance with an embodiment.
Figure 7:
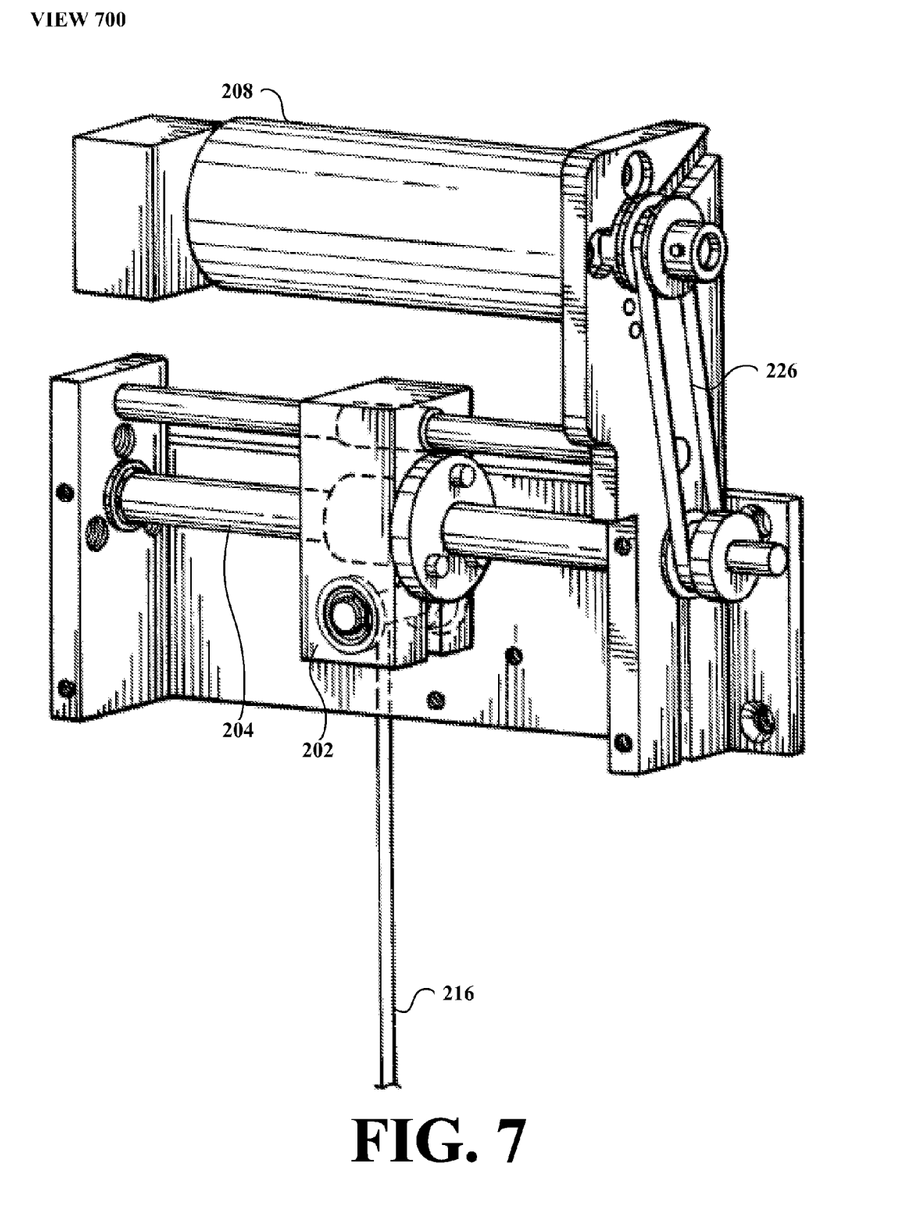
FIG. 7 depicts a carriage, rod, and displacement mechanism of the example gravity-compensation system, in accordance with an embodiment.

FIG. 5 depicts a third view 500 of gravity-compensation system 201, according to an example. In view 500, axis 206 has been rotated (from generally horizontal to angled) and carriage 202 has been moved on rod 204. As shown with reference to view 500, given the displacement of carriage 202, the direction of axis 214 has been rotated (from generally vertical to angled) as well. Note that the rotation of axis 206 may be primarily due to a user having rotated prismatic joint 109 in a generally upward direction. On the other hand, the rotation of axis 214 may be primarily due to a user having extended extendable arm 113, resulting in displacement mechanism 208 causing carriage 202 to move an amount that is proportional to the displacement of extendable arm 113.

As may be seen with reference to view 500, the geometry of gravity-compensation system 201 is chosen so that a linear spring (such as torsional spring 222C) can be used to exactly counter the weight of rotation of prismatic joint 109 in the x-y plane. The basic geometry is defined by a triangle composed of lengths "A," "B," and "C." Length C changes with rotation of prismatic joint 109 in the x-y plane for a given A, because length C is coupled with restorative-force mechanism 212, and it will stretch the springs in resistive-force mechanism 222 to produce a force in cable 216 acting on carriage 202. As the force on carriage 202 is increased (from increasing C), the moment arm of prismatic joint 109 decreases, maintaining a constant torque on prismatic joint 109.

Thus, if carriage 202 is driven a distance A along rod 204 proportional to the displacement of extendable arm 113 by a constant "c," then the necessary torsional spring constant to compensate for gravity may be defined as:

$$K = \frac{mgc}{B\Delta^2} \quad \text{Equation 1}$$

where m is the mass of extendable arm 113, B is the distance depicted in FIG. 5, and $\Delta$ is the gearing from the torque applied by resistive-force mechanism 212 to the force in cable 216.

Using trigonometry, the gravity-compensation torque required to achieve static balance of haptic device 100 can be determined according to the following equations:

$$A = \frac{(r-L)}{c} \quad \text{Equation 2}$$

$$C = \sqrt{A^2 + B^2 - 2AB\sin(\varphi)} \quad \text{Equation 3}$$

$$L_0 = \frac{R_C F_C}{K\Delta} \quad \text{Equation 4}$$

$$T_C = (R_C F_C + K(C-L_0)\Delta)\Delta \quad \text{Equation 5}$$

$$\tau_{gc\cdot\varphi} = \frac{T_C BA\cos\varphi}{c} \quad \text{Equation 6}$$

Where, r is the extension of extendable arm 113 from housing 111 to handle 115, L is the distance from the center of gravity of prismatic joint 109 to housing 111, $\varphi$ is the angle of rotation of prismatic joint 109 in the x-y plane, A and C are the distances depicted in FIG. 5, $T_C$ is the force applied by cable 216 on carriage 202 along axis 214, $R_C$ is the radius of gearing mechanism 222A, and $F_C$ is the force of constant-force spring 222B.

As a general matter, the magnitude of $F_C$ may be selected so as to create a zero initial spring length for torsional spring 222C. In this way, gravity-compensation system 212 may be preloaded and the required torsion spring deflection of torsion spring 222C may be decreased.

Note, also, that it may be generally desirable for restorative-force mechanism 212 be placed substantially directly below carriage 202 and/or the axis of rotation of housing 111 of prismatic joint 109. In this way, upon moving carriage 202 along rod 204, the force applied along axis 214 by cable 216 may act on prismatic joint 109 on the opposite side of the axis of rotation from that which the force of gravity acts. It may be possible to orient pulleys 228A and 228B so as to achieve this desired result.

III. Example Method

Figure 8:
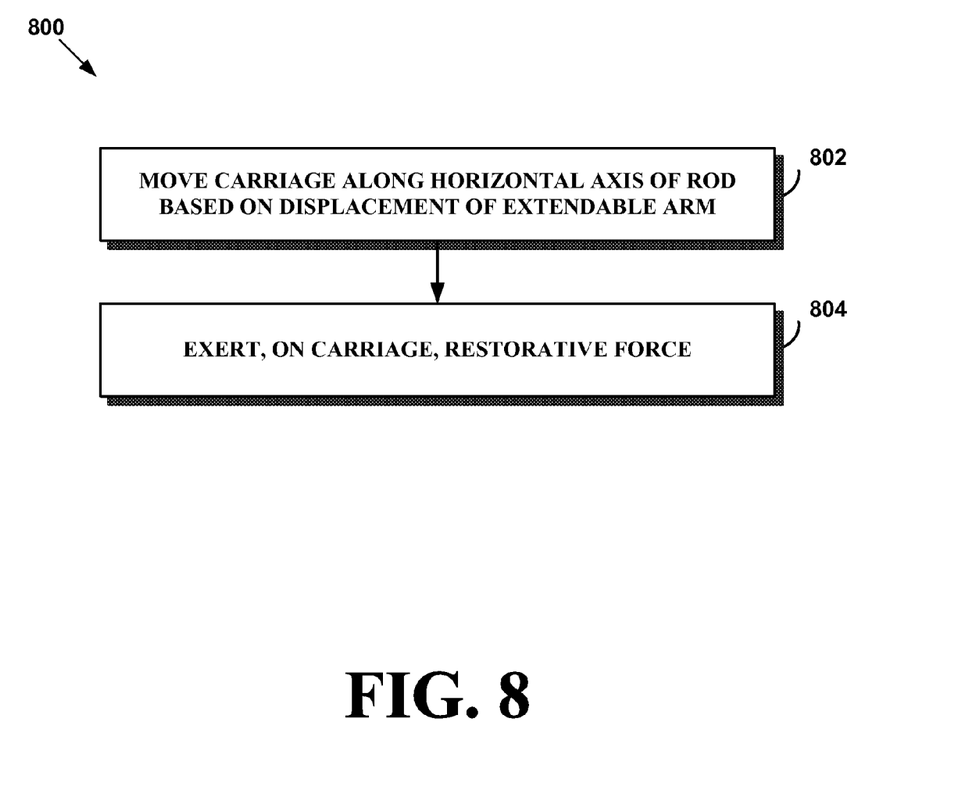
FIG. 8 depicts an example method for gravity compensation, in accordance with an embodiment.

FIG. 8 depicts an example method 800 for gravity compensation, in accordance with an embodiment. Example method 800 may be carried out by a gravity-compensation system, such as gravity-compensation system 201 as described herein.

Method 800 begins at step 802, where gravity-compensation system 201 moves carriage 202 along first axis 206 of rod 204 based on a displacement of extendable arm 113 along first axis 206. According to step 802, rod 204 may be a single-start lead screw. Additionally, carriage 202 may be moved along rod 204 by displacement mechanism 208, which may be a direct current (DC) motor.

At step 804, gravity-compensation mechanism 201 exerts, on carriage 202, restorative force $T_C$ that acts along second axis 214. Restorative-force mechanism 212 may exert restorative force $T_C$, and restorative-force mechanism may include cable 216 that has a first end coupled to carriage 202 and a second end that is coupled to gearing mechanism 218. Further, restorative-force mechanism 212 may include resistive-force mechanism 222 coupled to gearing mechanism 218. Resistive-force mechanism 222 may include at least one of a spring mechanism and a pneumatic mechanism. In the case that resistive-force mechanism 222 includes a spring mechanism, the spring mechanism may include at least one of constant-force spring 222B and torsion spring 222C.

IV. Conclusion

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope and spirit of the following claims and equivalents thereto are claimed as the invention.

We claim:

1. A system comprising:
    a carriage coupled to a rod having a first axis, wherein the carriage is configured to move along the first axis;
    a displacement mechanism coupled to the carriage, wherein the displacement mechanism is configured to move the carriage along the first axis of the rod based on a displacement of an extendable arm along the first axis; and
    a restorative-force mechanism configured to exert, on the carriage, a restorative force that acts along a second axis.

2. The system of claim 1, wherein the rod is a single-start lead screw.

3. The system of claim 1, wherein the restorative-force mechanism comprises:
    a cable having (i) a first end that is coupled to the carriage and (ii) a second end that is coupled to a gearing mechanism; and
    a resistive-force mechanism coupled to the gearing mechanism.

4. The system of claim 3, wherein the gearing mechanism comprises:
    a first gear, wherein the second end of the cable is coupled to the first gear; and
    a second gear coupled to (i) the first gear and (ii) the resistive-force mechanism.

5. The system of claim 3, wherein the resistive-force mechanism comprises at least one of a spring mechanism and a pneumatic mechanism.

6. The system of claim 5, wherein the resistive-force mechanism comprises the spring mechanism, and wherein the spring mechanism comprises at least one of a constant-force spring and a torsion spring.

7. The system of claim 3, wherein the restorative-force mechanism further comprises:
    a pulley mechanism positioned between the carriage and the gearing mechanism, wherein the pulley mechanism is configured to direct the restorative force along the second axis.

8. The system of claim 1, wherein the displacement mechanism comprises a direct current (DC) motor.

9. The system of claim 1, wherein the displacement mechanism is further configured to move the carriage along the horizontal axis proportional to the displacement of the extendable arm along the first axis.

10. The system of claim 1, further comprising:
    a prismatic joint wherein the rod, carriage, and displacement mechanism are attached to an exterior of the prismatic joint, and wherein the extendable arm extends through an interior of the prismatic joint.

11. The system of claim 10, wherein the extendable arm is a telescoping extendable arm.

12. The system of claim 10, the system further comprising:
    a turret section that is rotatable about a third axis, wherein the prismatic joint is affixed atop the turret section such that the extendable arm is rotatable about the third axis.

13. The system of claim 10, wherein the extendable arm is rotatable about a third axis that is perpendicular to the first axis and the second axis.

14. A method comprising:
    moving a carriage along a first axis of a rod based on a displacement of an extendable arm along the first axis; and
    exerting, on the carriage, a restorative force that acts along a second axis.

15. The method of claim 14, wherein the rod is a single-start lead screw.

16. The method of claim 14, wherein exerting, on the carriage, a restorative force, comprises a restorative-force mechanism exerting, on the carriage, the restorative force, wherein the restorative-force mechanism comprises:
    a cable having (i) a first end that is coupled to the carriage and (ii) a second end that is coupled to a gearing mechanism; and
    a resistive-force mechanism coupled to the gearing mechanism.

17. The method of claim 16, wherein the gearing mechanism comprises:
   a first gear, wherein the second end of the cable is coupled to the first gear; and
   a second gear coupled to (i) the first gear and (ii) the resistive-force mechanism.

18. The method of claim 16, wherein the resistive-force mechanism comprises at least one of a spring mechanism and a pneumatic mechanism.

19. The method of claim 16, wherein the resistive-force mechanism comprises the spring mechanism, and wherein the spring mechanism comprises at least one of a constant-force spring and a torsion spring.

20. The method of claim 14, wherein moving the carriage along the first axis of the rod comprises a direct current (DC) motor moving the carriage along the first axis of the rod.

* * * * *